(12) United States Patent
Soares Da Costa et al.

(10) Patent No.: US 9,259,304 B2
(45) Date of Patent: Feb. 16, 2016

(54) METHOD OF MENDING A GROIN DEFECT

(71) Applicant: Bard Shannon Limited, Humacao, PR (US)

(72) Inventors: Rui Manuel De Melo Soares Da Costa, Porto (PT); Augusto Manuel De Almeida Lourenço, Guarda (PT)

(73) Assignee: Bard Shannon Limited, Humacao, PR (US)

( * ) Notice: Subject to any disclaimer, the term of this patent is extended or adjusted under 35 U.S.C. 154(b) by 0 days.

(21) Appl. No.: 14/660,747

(22) Filed: Mar. 17, 2015

(65) Prior Publication Data

US 2015/0182323 A1    Jul. 2, 2015

Related U.S. Application Data

(60) Continuation of application No. 14/480,690, filed on Sep. 9, 2014, now Pat. No. 9,011,552, which is a division of application No. 13/544,072, filed on Jul. 9, 2012, now Pat. No. 9,011,550.

(51) Int. Cl.
*A61F 2/02* (2006.01)
*A61F 2/00* (2006.01)

(52) U.S. Cl.
CPC .......... *A61F 2/0063* (2013.01); *A61F 2002/009* (2013.01); *A61F 2002/0086* (2013.01); *A61F 2250/006* (2013.01)

(58) Field of Classification Search
CPC ............... A61B 2017/00637; A61B 2250/006; A61B 19/00; A61F 2/0063; A61F 2/08; A61F 2002/009
See application file for complete search history.

(56) References Cited

U.S. PATENT DOCUMENTS

| | | | |
|---|---|---|---|
| 5,220,928 A * | 6/1993 | Oddsen et al. | 128/898 |
| 5,540,711 A * | 7/1996 | Kieturakis et al. | 606/192 |
| 5,634,931 A | 6/1997 | Kugel | |
| 5,716,409 A | 2/1998 | Debbas | |
| 5,769,864 A | 6/1998 | Kugel | |
| 5,916,225 A | 6/1999 | Kugel | |
| 5,954,767 A | 9/1999 | Pajotin et al. | |
| 6,166,286 A | 12/2000 | Trabucco | |
| 6,171,318 B1 | 1/2001 | Kugel et al. | |

(Continued)

OTHER PUBLICATIONS

*Hernia* (2009), p. S43-S44.

(Continued)

*Primary Examiner* — Victor Nguyen
(74) *Attorney, Agent, or Firm* — Wolf, Greenfield & Sacks, P.C.

(57) ABSTRACT

A method of mending a groin defect such as an indirect inguinal hernia, a direct inguinal hernia, and/or a femoral hernia. A space between the external oblique aponeurosis and the internal oblique aponeurosis is dissected superiorly and laterally to create a site for receiving a lateral portion of a prosthetic repair patch. Dissection medially and inferiorly between the two aponeuroses leads to a transversalis fascia, which is explored downwardly and, at the pubic bone, dissected to reach the preperitoneal space of Retzius. A medial portion of a prosthetic repair patch may be positioned in the space of Retzius with a lateral portion of the prosthetic repair patch positioned in the dissected space between the two aponeuroses. So positioned, the prosthetic repair patch protects the myopectineal orifice that is susceptible to each of the indirect inguinal hernia, direct inguinal hernia, and femoral hernia.

8 Claims, 3 Drawing Sheets

(56) References Cited

U.S. PATENT DOCUMENTS

| | | | |
|---|---|---|---|
| 6,174,320 B1 | 1/2001 | Kugel et al. |
| 6,214,020 B1 | 4/2001 | Mulhauser et al. |
| 6,224,616 B1 | 5/2001 | Kugel |
| 6,258,124 B1 | 7/2001 | Darois et al. |
| 6,280,453 B1 | 8/2001 | Kugel et al. |
| 6,290,708 B1 | 9/2001 | Kugel et al. |
| 6,497,650 B1 | 12/2002 | Nicolo |
| 6,565,580 B1 | 5/2003 | Beretta |
| 6,652,595 B1 | 11/2003 | Nicolo |
| 6,669,735 B1 | 12/2003 | Pelissier |
| 6,723,133 B1 | 4/2004 | Pajotin |
| 6,736,823 B2 | 5/2004 | Darois et al. |
| 6,740,122 B1 | 5/2004 | Pajotin |
| 6,790,213 B2 | 9/2004 | Cherok et al. |
| 7,156,804 B2 | 1/2007 | Nicolo |
| 7,404,819 B1 | 7/2008 | Darois et al. |
| 7,824,420 B2 | 11/2010 | Eldridge et al. |
| 8,182,545 B2 | 5/2012 | Cherok et al. |
| 2001/0049538 A1 | 12/2001 | Trabucco |
| 2004/0073257 A1 | 4/2004 | Spitz |
| 2004/0181288 A1 | 9/2004 | Darois et al. |
| 2005/0159777 A1 | 7/2005 | Spitz |
| 2006/0064175 A1 | 3/2006 | Pelissier et al. |
| 2007/0032881 A1 | 2/2007 | Browning |
| 2007/0225804 A1 | 9/2007 | Checa Ayet |
| 2011/0208217 A1 | 8/2011 | Checa Ayet |
| 2012/0078274 A1 | 3/2012 | Nicolo |

OTHER PUBLICATIONS

Lourenco et al., "Open TEP—The Procedure Made Simpler—Our Experience," 2009 Joint Meeting, Berlin, Sep. 9-12, 10 pages.

Rosenberg et al., "ONSTEP Technique fo r Inguinal Hernia Repair," Mar. 29, 2012, New York, NY, 42 pages.

* cited by examiner

METHOD OF MENDING A GROIN DEFECT

RELATED APPLICATIONS

This application claims the benefit under 35 U.S.C. §120 of U.S. application Ser. No. 14/480,690, entitled "METHOD OF MENDING A GROIN DEFECT" filed on Sep. 9, 2014, which is herein incorporated by reference in its entirety. Application Ser. No. 14/480,690 claims the benefit under 35 U.S.C. §120 of U.S. application Ser. No. 13/544,072, entitled "METHOD OF MENDING A GROIN DEFECT" filed on Jul. 9, 2012, which is herein incorporated by reference in its entirety.

FIELD

The field relates to surgical procedures and, more specifically, to a surgical method for mending a groin defect.

BACKGROUND

Groin hernias are typically characterized as indirect inguinal hernias, direct inguinal hernias, and femoral hernias. It is known to repair such hernias by covering the defect with a prosthetic repair patch. In the classic 'Lichtenstein' procedure, the patch is placed anteriorly of the transversalis fascia. Alternatively, the patch may be positioned posteriorly of the transversalis fascia, between the transversalis fascia and the peritoneum—this location being known as the 'preperitoneal space'. A prosthetic repair patch may be delivered laparoscopically to the preperitoneal space in a procedure known as TEP—"Totally Extra Peritoneal". Alternatively, a prosthetic repair patch may be placed in the preperitoneal space via an 'open' procedure. Two common open procedures for preperitoneal placement of a prosthetic repair patch include the POLYSOFT Hernia Patch procedure and the Kugel procedure. In the POLYSOFT approach, access to the preperitoneal space is through the defect itself. In the Kugel procedure, an opening is formed directly through the three layers overlying the preperitoneal space—the external oblique aponeurosis, the internal oblique aponeurosis, and the transversalis fascia. In both the POLYSOFT procedure and the Kugel procedure, the prosthetic repair patch is positioned in a single tissue plane between the peritoneum and the transversalis fascia.

SUMMARY

Methods are provided for mending a groin defect, specifically defects of the myopectineal orifice including an indirect inguinal hernia, direct inguinal hernia, and/or a femoral hernia. In certain aspects, a method is provided for reaching a preperitoneal space without having to penetrate through a groin defect and without having to dissect through the internal oblique aponeurosis. In other aspects, a method of repairing a groin defect is provided where a prosthetic repair patch is positioned in two different tissue planes in the groin region; only one of the tissue planes being preperitoneal.

In one embodiment, a method of mending a groin defect includes dissecting inferiorly between an external oblique aponeurosis and an internal oblique aponeurosis to reach the transversalis fascia, and then dissecting through the transversalis fascia at the area of the pubic bone into the preperitoneal space, such as the space of Retzius. The method may further include implanting a prosthetic repair patch that extends from the preperitoneal space to the dissected area between the external oblique aponeurosis and an internal oblique aponeurosis.

In another embodiment, a method of mending a groin defect includes positioning a medial portion of a prosthetic repair patch posteriorly of a transversalis fascia in a preperitoneal space, and positioning a lateral portion of the prosthetic repair patch anteriorly of the transversalis fascia. More particularly, the method may include an open procedure where a lateral portion of the prosthetic repair patch is placed in a surgically created space between the external oblique aponeurosis and the internal oblique aponeurosis, and a medial portion of the prosthetic repair patch is placed in the space of Retzius.

In a further embodiment, a method of mending a groin defect includes, in an open procedure, creating an access through a transversalis fascia and into a preperitoneal space, such as the space of Retzius, and then positioning a portion of a prosthetic repair patch in the preperitoneal space and another portion of the prosthetic repair patch anteriorly of the transversalis fascia.

The foregoing is a non-limiting summary of the invention, which is defined by the attached claims. Other aspects, embodiments, features will become apparent from the following description.

BRIEF DESCRIPTION OF DRAWINGS

Various embodiments of the invention will now be described, by way of example, with reference to the accompanying drawings, in which.

DETAILED DESCRIPTION

Figure 1:
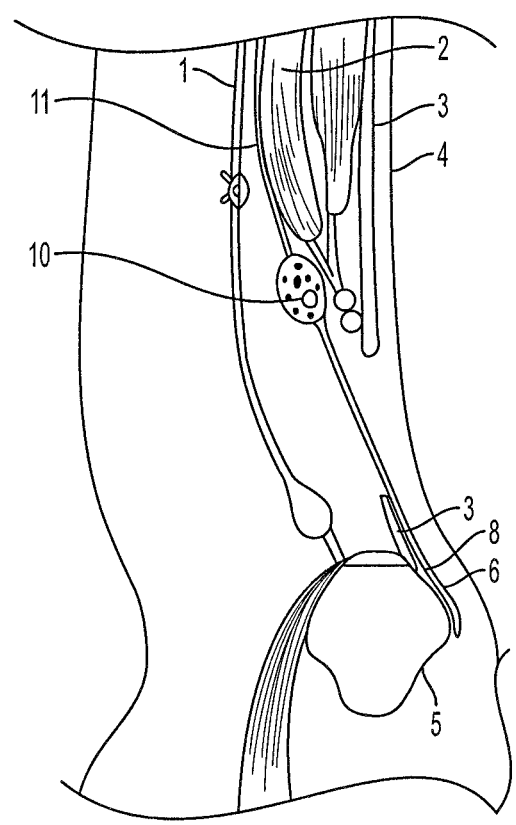
FIG. 1 is an illustration of a prosthetic repair patch extending from behind the pubic bone in the space of Retzius to a dissected space between the external oblique aponeurosis and the internal oblique aponeurosis.

It should be understood that aspects of the invention are described herein with reference to the figures, which show illustrative embodiments in accordance with aspects of the invention. The illustrative embodiments described herein are not necessarily intended to show all aspects of the invention, but rather are used to describe a few illustrative embodiments. Thus, aspects of the invention are not intended to be construed narrowly in view of the illustrative embodiments. It should be appreciated, then, that the various concepts and embodiments discussed herein may be implemented in any of numerous ways, as the disclosed concepts and embodiments are not limited to any particular manner of implementation. In addition, it should be understood that aspects of the invention may be used alone or in any suitable combination with other aspects of the invention.

An open procedure is described for mending a groin defect including, but not limited to, one or more of an indirect inguinal hernia, a direct inguinal hernia, a femoral hernia and/or other weakness or rupture of the groin anatomy. The phrase "mending a groin defect" includes acts of repairing, augmenting, and/or reconstructing a groin defect and/or a potential groin defect. Although the open procedure is described in connection with placing a prosthetic repair patch at the defect site, the treatment is not so limited and other medical responses to a defect of the groin that employ the surgically created pathway disclosed herein also are contemplated.

In one embodiment, an open procedure creates a space between the external oblique aponeurosis 1 and the internal oblique aponeurosis 2 superiorly and laterally to an incision site. This space may be configured to receive a lateral portion 11 of a prosthetic repair patch. Medially and inferiorly of the dissected space between the two oblique aponeuroses, and remote from the groin defect, the transversalis fascia 3 is penetrated to reach the space of Retzius 8—an area located deep of the pubic bone 5 and anteriorly of the peritoneum 4. A surgically created pathway now runs from the space of Retzius 8, a preperitoneal space, to the dissected area between the external oblique aponeurosis 1 and the internal oblique aponeurosis 2. A patch may be implanted along this pathway, with a lateral portion 11 positioned in the dissected space between the external oblique aponeurosis and the internal oblique aponeurosis and a medial portion 6 extending through the transversalis fascia to the preperitoneal area of the pubic bone 5. An intermediate portion runs with the spermatic cord, extending transversely between the medial and lateral portions of the prosthetic repair patch. A slit may be provided in the lateral portion to define two separable portions, referred to as "tails", that may be spread apart to accommodate the spermatic cord. Subsequently, the tails are reunited and, if desired, sutured together or otherwise secured.

More specifically, a representative procedure for treating an inguinal hernia, whether an indirect or direct inguinal hernia, will now be described. A small transverse incision, approximately 3 cm long, is made about two fingers breadths above and lateral to the pubic synthesis. The incision is lateral to the rectus muscles and avoids the superficial anterior branches of the iliohypogastric nerve and the femoral branch of the genitofemoral nerve. The anterior surface of Scarpa's fascia is then exposed. Blunt dissection of Scarpa's fascia exposes the anterior surface of the external oblique aponeurosis 1. Further dissection of the external oblique aponeurosis exposes the underlying internal oblique aponeurosis 2—which is not dissected or otherwise opened. Dissection proceeds between the two oblique aponeuroses laterally and superiorly to approximately the superior iliac spine; for example, the surgeon's finger may be swept between the respective tissue planes, creating a space to receive a lateral portion 11 of a prosthetic repair patch. Medially, a probing finger facing upwards is swept to identify the spermatic cord 10, which is then elevated out of the incision. The cord is explored for the presence of an indirect hernia and, if found, the sac contents are reduced and the excess sac ligated or removed as appropriate. If a direct hernia is identified, the sac and contents may be reduced into the abdominal cavity. The transversalis fascia 3 is then digitally explored down to the public bone 5. Here, the transversalis fascia 3 is penetrated, for example, by plunging the surgeon's finger through the fascia to create an opening that leads to the preperitoneal space of Retzius 8. The space of Retzius 8 may be dissected to configure the location for receipt of a medial portion 6 of a prosthetic repair patch. A sterile gauze may be inserted into the incision and advanced down towards the pubic bone to bluntly dissect the space that will receive the prosthetic repair patch.

Figure 2:
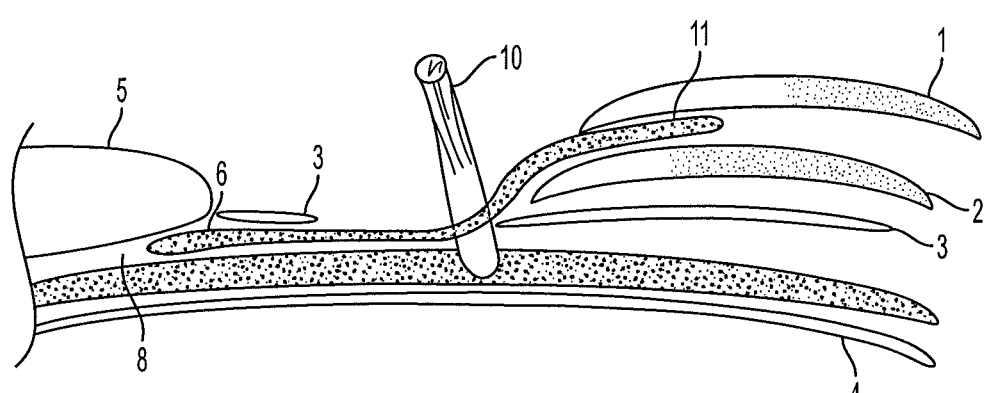
FIG. 2 is another illustration of a prosthetic repair patch implanted according to the present procedure.

A medial portion 6 of a prosthetic repair patch can now be advanced down the surgically created access to the preperitoneal space of Retzius 8 behind the pubic bone 5, while a lateral portion 11 of the patch can now be located in the dissected space between the external and internal oblique aponeuroses. An intermediate portion of the patch runs down from the lateral portion along the spermatic cord 10 and posteriorly of the transversalis fascia 3 to the medial portion 6, such that the implanted patch may approximate an S-shape as shown in FIG. 2. The patch should be sufficiently flexible to allow placement of portions of the patch in and along these different tissue planes. No fixation of the medial or lateral portions of the patch is required. With the prosthetic repair patch in place and covering one or more of the groin defects of interest and, in certain embodiments, completely protecting the myopectineal orifice so as to extend about all of the areas susceptible to indirect inguinal hernia, direct inguinal hernia and femoral hernia, the external oblique aponeurosis and the initial incision may be closed, such as by suturing, stapling and the like.

Figure 3:
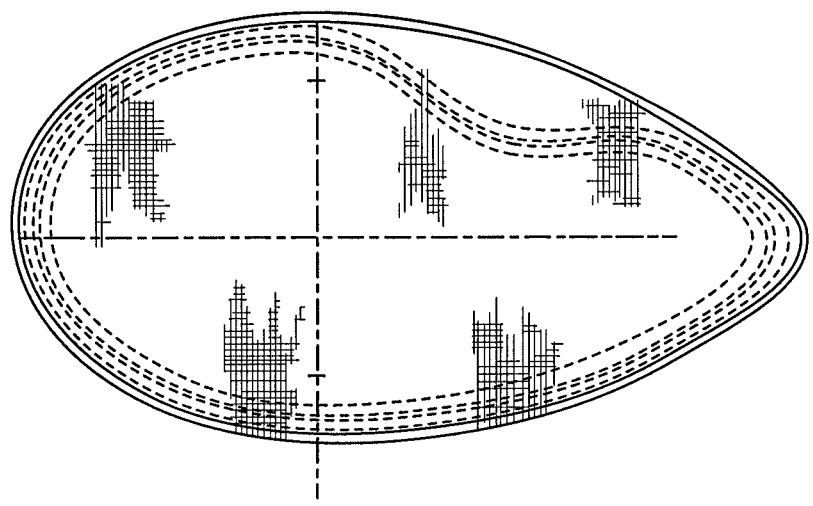
FIG. 3 is an illustration of a representative repair patch for use in the disclosed procedure for mending a groin defect.

A representative prosthetic repair patch suitable for use in this procedure includes the POLYSOFT Hernia Patch available from Davol Inc., a subsidiary of C.R. Bard, Inc. The POLYSOFT Hernia Patch includes a body portion of tissue infiltratable knit fabric, such as BARD MESH, and an interrupted memory recoil ring that is integrated with the body portion to facilitate manipulation and deployment of the patch. A slit may be provided in the patch between the interrupted ends of the ring to create a pair of separable tails for accommodating the spermatic cord. The POLYSOFT Hernia Patch is sized to protect the myopectineal orifice and, thus, the anatomy susceptible to indirect hernia, direct hernia and femoral hernia; however, patches that are configured to protect only one or more of these groin regions of interest also are contemplated. The POLYSOFT Hernia Patch, a planar-type patch with an oval configuration, is shown in FIG. 3.

The patch may be formed of any fabric suitable for repair or augmentation of a soft tissue defect. Without limiting the foregoing, the fabric may constitute a resorbable material, a permanent material, or a hybrid of resorbable and permanent materials. Non-limiting examples of resorbable fabric materials include resorbable polyesters such as polyglycolic acid (PGA), polylactic acid (PLA), poly(lactic-co-glycolic acid) (PLGA), polydioxanone (PDO), polycaprolactone (PCL), any other resorbable polyester, polyhydroxyalkanoate (PHA), as well as collagen, calcium alginate and combinations of any of the foregoing. Permanent fabric materials include polypropylene, polyethylene, polyester, polytetrafluoroethylene, and other non-resorbable polymers having application in soft tissue repair fabrics. Some or all of the patch may be configured to promote tissue ingrowth into interstices of the patch and/or around the patch, or to discourage same. Thus, the patch may be porous, micro-porous, or essentially non-porous, and different regions of the patch may have different porosity characteristics. If desired some or all of the surfaces of the patch may include a barrier that is resistant to adhesions with sensitive organs or tissue. The patch may be loaded with one or more medicinal or therapeutic agents including, but not limited to, an analgesic or antibiotic. The patch may be formed of one or more layers, with the layers having the same or different properties including, but not limited to, material composition. The patch may in the form of a planar-like sheet, and may be configured with convexity, concavity, a combination of convexity and concavity, and other shapes. As observed earlier, the patch may be flexible to facilitate placement of portions of the patch in different tissue planes. As in the POLYSOFT Hernia Patch, the patch for use in the disclosed methodology may include a ring or other support feature to aid in handling and deployment thereof. Such a ring may be made of a permanent or a resorbable material.

It should be understood that the foregoing description of various embodiments of the invention are intended merely to be illustrative thereof and that other embodiments, modifications, and equivalents of the invention are within the scope of the invention recited in the claims appended hereto.

What is claimed is:

1. A method of mending a groin defect, comprising the acts of:
creating an incision superior and lateral to the pubic synthesis;
externalizing a spermatic cord through the incision;
locating the spermatic cord between two separable portions of a prosthetic repair patch;
implanting a lateral portion of the prosthetic repair patch at a first tissue plane in a groin region; and
implanting a medial portion of the prosthetic repair patch at a second tissue plane in the groin region, the second tissue plane being posterior to the first tissue plane.

2. The method recited in claim 1, wherein the act of locating includes spreading apart separable portions of a lateral portion of the prosthetic repair patch.

3. The method recited in claim 2, further comprising the act of securing the separable portions together after they have been spread apart and the spermatic cord located therebetween.

4. The method recited in claim 1, wherein the lateral portion implanting act and the medial portion implanting act include forming the prosthetic repair patch into an S-shape.

5. The method recited in claim 1, wherein the first tissue plane is anterior of a transversalis fascia.

6. The method recited in claim 5, where the first tissue plane is between the external oblique aponeurosis and the internal oblique aponeurosis.

7. The method recited in claim 1, where the second tissue plane is posterior of a transversalis fascia.

8. The method recited in claim 7, wherein the second tissue plane is preperitoneal.

* * * * *